United States Patent [19]

Lehmann et al.

[11] 4,313,831
[45] Feb. 2, 1982

[54] PROCESS AND DEVICE FOR THE REMOVAL OF WASTE METABOLITES FROM A SOLUTION CONTAINING SUCH METABOLITES

[75] Inventors: Hans-Dieter Lehmann, Hechingen, Fed. Rep. of Germany; Lars-Ake Larsson, Loddekopinge, Sweden

[73] Assignees: Gambro Dialysatoren KG, Fed. Rep. of Germany; Gambro AB, Sweden

[21] Appl. No.: 104,446

[22] Filed: Dec. 17, 1979

[30] Foreign Application Priority Data

Jan. 4, 1979 [SE] Sweden ............................ 7900063

[51] Int. Cl.³ .............................................. B01D 13/00
[52] U.S. Cl. ................................... 210/646; 210/648; 210/677
[58] Field of Search .................. 210/34, 321 B, 22 A, 210/264, 648, 646, 677, 691

[56] References Cited

U.S. PATENT DOCUMENTS 1,985,205 12/1934 Perr .................................. 210/264 X
3,697,418 10/1972 Johnson ........................... 210/34 X
4,118,314 10/1978 Yoshida ....................... 210/321 B X

*Primary Examiner*—Frank A. Spear, Jr.
*Attorney, Agent, or Firm*—Lerner, David, Littenberg & Samuel

[57] ABSTRACT

Processes and apparatus for the removal of waste metabolites from metabolite-containing solutions are disclosed. The disclosed processes include alternatively adsorbing and desorbing the metabolites on a pair of adsorbent-containing columns, each column being maintained at a reduced temperature during adsorption and at an elevated temperature during desorption, with the columns being flushed subsequent to desorption and prior to their re-use for adsorption thereon. The disclosed apparatus includes a pair of adsorbent-containing columns, means for alternatively delivering the metabolite containing solution to each of the columns for alternate adsorption and desorption thereon, means for withdrawing the metabolite containing solution from each of the columns, means for alternately flushing the columns subsequent to desorption and prior to adsorption thereon, and means for alternately maintaining the columns at reduced temperatures during adsorption and at elevated temperatures during desorption so that the effectiveness of the adsorbent for adsorption is increased during adsorption at the reduced temperatures.

A disposable tube set for use in connection with such a pair of adsorbent containing columns is also disclosed, including a flexible inlet tube including a pair of inlet branches for delivery of the metabolite containing solution to each of the columns, and a flexible outlet tube including a pair of outlet tube branches for connection with the outlet end of each of the columns.

12 Claims, 2 Drawing Figures

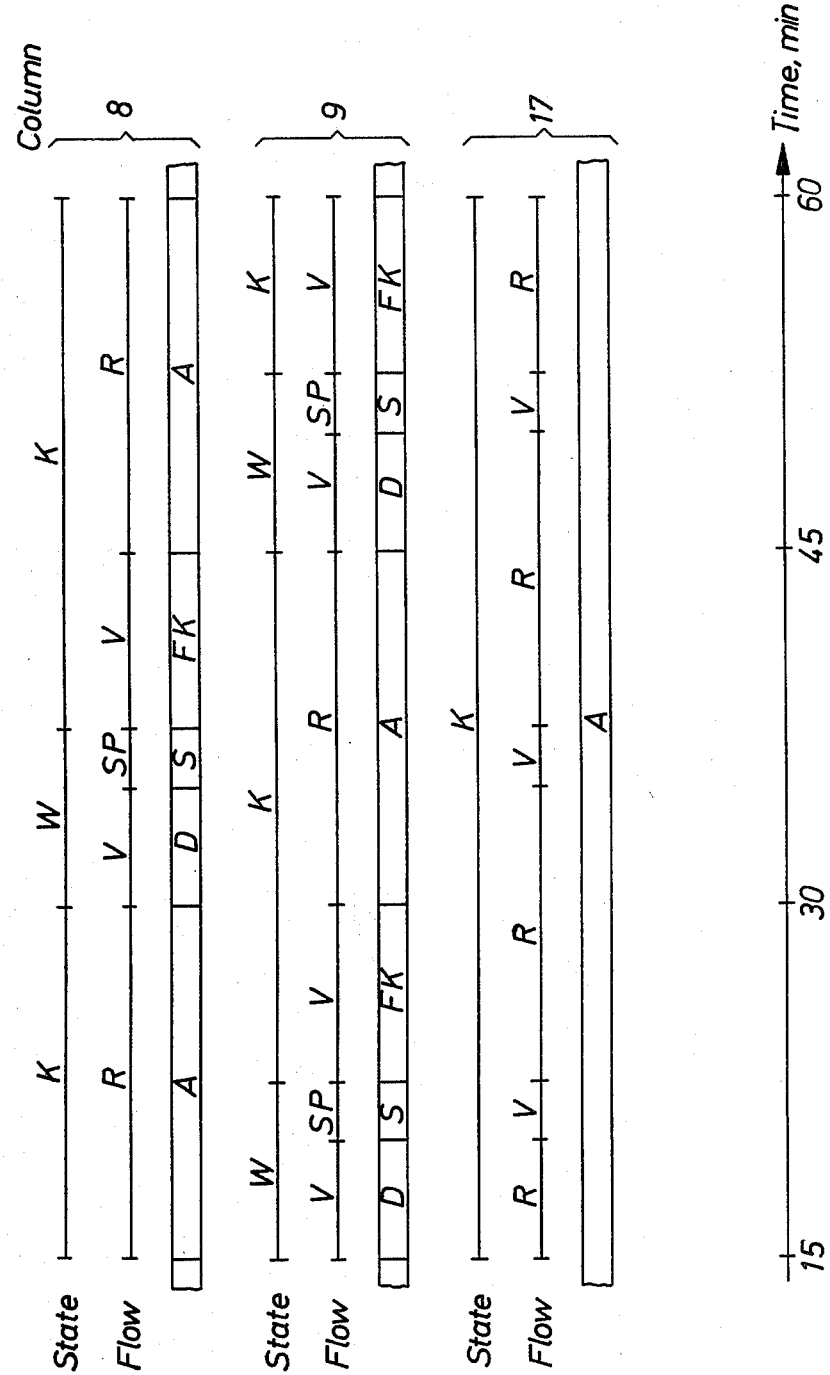

PROCESS AND DEVICE FOR THE REMOVAL OF WASTE METABOLITES FROM A SOLUTION CONTAINING SUCH METABOLITES

FIELD OF THE INVENTION

The present invention relates to apparatus and processes for the removal of waste metabolites, especially nitrogenous poisons, from metabolite containing solutions. More particularly, the present invention relates to processes and apparatus for the removal of waste metabolites such as urea from a hemofiltrate or the like of a patient suffering from uremia. Still more particularly, the present invention also relates to disposable tube sets adapted to be used in such devices and for carrying out such processes.

BACKGROUND OF THE INVENTION

Various systems are known for use in connection with the removal of waste metabolites from metabolite containing solutions. In this connection the expression "waste metabolites" is used in order to include all possible harmful metabolites, which cannot be released from the patient naturally, and which therefore have to be eliminated artificially. Furthermore, this expression is also meant to include electrolytes, such as potassium, which in uremic patients is present in abnormally high concentrations.

It is known that urea, which is an example of a waste metabolite, is only adsorbed poorly onto activated carbon at 37° C. For the removal of between 20 and 30 grams of urea per treatment large amounts of adsorbent (activated carbon) are thus required. Compare C. Giordano, R. Esposito, Report PB 255 495, pp. 25-41 (19.3.76), which does include a recognition of the temperature dependence of such adsorption. Such adsorption can be improved by using low temperatures, but even near 0° C. the amount of urea to be removed requires large amounts of activated carbon (e.g., between 1.5 and 2 kg, on a dry basis). From the point of view of economics, regeneration of the adsorbent is necessary. Furthermore, the handling and disposal of these large amounts of carbon, which together with the water present in the used columns amounts to between 4 and 5 kg, is troublesome.

One prior art system which is based on the fact that urea is adsorbed on activated carbon to a higher degree at a lower temperature, and which comprises regeneration of the activated carbon, is described in the U.S. Pat. No. 3,697,418. In this system large volumes of liquid (between 13 and 26 liters) are required for the total treatment, inclusive of regeneration, while at the same time the time per treatment is long (e.g., 10 hours). For regeneration, cooled and purified solution is used, so that adsorption and desorption (i.e., regeneration) are strictly time-alternated, i.e., equal times are needed for the adsorption and the desorption, and they are performed in serially coupled columns.

The object of the present invention is to provide a process and apparatus which is also based upon the temperature-dependent adsorption capability of an adsorbent, but which can reduce the required treatment time, as well as the amount of spent solution per treatment. In contrast to the process shown in U.S. Pat. No. 3,697,418, for example, it is desired to be able to take into account the well-known fact that the diffusion rates of the reversibly adsorbed metabolite urea, for example, is much higher at high temperatures than at low temperatures. The desorption time can therefore be reduced in favor of the adsorption phases, which are at present limiting the efficiency of such devices.

SUMMARY OF THE INVENTION

In accordance with the present invention, processes and apparatus have now been discovered by which it is possible to reduce the required treatment time to from 3 to 4 hours with only 2.5 to 4.5 liters of solution per treatment being spent for the removal of between 20 and 30 grams of urea, for example, from a hemofiltrate. Furthermore, compensation for this relatively small amount of solution can be easily made. These results are primarily obtained in accordance with the process and apparatus of improved efficiency hereof by performing in parallel and at the same time both adsorption and desorption (or regeneration), in which the desorption includes warming, flushing, and pre-cooling, and wherein flushing is carried out by preferably using the same solution as that from which the waste metabolites are to be removed.

In accordance with the apparatus of the present invention, the removal of waste metabolites from a metabolite-containing solution is effected by alternately adsorbing and desorbing the metabolites on an adsorbent contained in a plurality of adsorbent containing columns, employing an apparatus comprising first and second columns containing an adsorbent for the metabolites, delivery conduit means for alternately delivering the metabolite-containing solution to the first and second columns so as to alternately adsorb and desorb the metabolite on the adsorbent in the columns, the adsorption occurring in the first and second columns, respectively, during delivery of the metabolite-containing solution to that column, and said metabolite-containing solution remaining in contact with the adsorbent during the desorption thereof, withdrawal conduit means for alternately withdrawing the metabolite-containing solution from the first and second columns, flushing conduit means for alternately flushing the columns with a flushing liquid when the metabolites are being adsorbed in the alternate columns, and temperature control means for alternately maintaining the columns at a first predetermined temperature and a second predetermined temperature, respectively, during adsorption and desorption thereof, the first predetermined temperature being lower than the second predetermined temperature in order to increase the effectiveness of the adsorbent for adsorption during such adsorption at the first temperature.

In accordance with one embodiment of the apparatus of the present invention, the temperature control means includes means for lowering the second predetermined temperature subsequent to desorption of the metabolite in the column in order to pre-cool the columns prior to carrying out adsorption therein.

In accordance with another embodiment of the apparatus of the present invention, delivery control means are provided for terminating the delivery of the metabolite containing solution to the columns prior to flushing the columns so that desorption of the columns is carried out substantially without the flow of liquid therethrough.

In accordance with a preferred embodiment of the present invention, a third adsorbent containing column is employed, the third column being associated with the delivery conduit means so that metabolites are adsorbed therein prior to delivery of the metabolite containing solution to the first and second columns. Preferably the third column is maintained substantially at the first predetermined temperature.

In accordance with a preferred embodiment of the present invention, the adsorbent utilized comprises activated carbon and the metabolite comprises nitrogenous poisons. Preferably, the activated carbon used is in the form of cylindrical rods, which are preferably relatively short in length.

In accordance with a preferred embodiment of the present invention, the flushing conduit means comprises a shunt conduit coupled in parallel to the delivery conduit means so that the first and second columns can be flushed with the flushing liquid between desorption and adsorption of the columns. Preferably flush withdrawal conduit means are provided for withdrawal of the flushing liquid from the first and second columns, and also provided are flush liquid collection means for collecting the flush liquid withdrawn from the columns.

In another embodiment of the apparatus of the present invention, the temperature control means include heat exchange containers in contact with the columns so that heat exchange fluids can be passed into the heat exchange containers in order to control the temperature of the columns. Preferably, in this embodiment heat exchange fluid control means for alternately feeding a cooling liquid and a heating liquid into the heat exchange containers associated with the first and second columns in order to alternately establish the first and second predetermined temperatures in those columns are provided.

In accordance with another embodiment of the present invention, pre-cooling means are provided associated with the delivery conduit means for pre-cooling the metabolite containing solution prior to its delivery into the first and second columns. Preferably, the pre-cooling means includes a heat exchanger, and the heat exchanger is also associated with the withdrawal conduit means in order to simultaneously warm the solution withdrawn from the columns as well as pre-cool the solution being fed to the columns.

In accordance with another embodiment of the apparatus of the present invention, buffering liquid container means are provided which are connectable with the withdrawal conduit means so that a buffering liquid comprising a predetermined buffering volume of the metabolite containing solution can be added to that solution in the withdrawal conduit means.

In another embodiment of the present invention, flushing liquid weighing means for weighing the flushing liquid contained in the flushing liquid container, and buffering liquid weighing means for weighing the buffering liquid contained in the buffering liquid container means are also provided.

In accordance with a preferred embodiment of the present invention, both the delivery conduit means and the withdrawal conduit means are formed from flexible plastic tubing.

In accordance with another embodiment of the present invention, the delivery control means comprises a pair of valves associated with the delivery conduit means for terminating the flow of the metabolite-containing solution into the first and second columns, respectively. Preferably, the delivery conduit means includes a separate conduit branch for each of the first and second columns and the valves are associated with each of those separate conduit branches.

In accordance with another embodiment of the apparatus of the present invention, shunt conduit control means associated with the shunt conduit are provided for controlling the flow of the metabolite containing solution through the shunt conduit so that substantially all of the metabolite-containing solution can be used as the flushing liquid in the columns when the delivery control means has terminated the delivery of the metabolite containing solution to those columns.

In accordance with the process of the present invention for removal of waste metabolites from a metabolite-containing solution, the process comprises alternately delivering the metabolite-containing solution to first and second adsorbent containing columns to alternately adsorb and desorb the metabolites on the adsorbent in those columns, with the metabolite being adsorbed on the adsorbent during delivery of the metabolite-containing solution to the columns and with the metabolite-containing solution remaining in contact with the adsorbent during desorption of the columns, maintaining the first and second columns at a first predetermined temperature during adsorption and at a second predetermined temperature during desorption, the first predetermined temperature being lower than the second predetermined temperature, so as to increase the effectiveness of the adsorbent for adsorption of the metabolite on the adsorbent at that first predetermined temperature, and flushing the first and second columns with a flushing solution subsequent to desorption thereof.

In a preferred embodiment of the process of the present invention subsequent to desorption of each column the second predetermined temperature is lowered in order to pre-cool the columns prior to adsorbing the metabolite in the first and second columns at the first temperature.

In accordance with a preferred embodiment of the process of the present invention, flow of the metabolite containing solution to the first and second columns, respectively, is terminated prior to flushing the column so that desorption of the column is carried out substantially without the flow of any liquid therein.

In accordance with another embodiment of the process of the present invention the first and second columns are maintained at the first predetermined temperature for a first predetermined time period and the columns are maintained at the second predetermined temperature for a second predetermined time period, the second predetermined time period being shorter than the first predetermined time period. Preferably the second predetermined time period will be less than about 75% of the first predetermined time period, and most preferably from about 20% to 50% of the first predetermined time period.

In accordance with another embodiment of the present invention, only a minor portion of the metabolite-containing solution contacts the adsorbent during desorption of the columns.

In accordance with a preferred embodiment of the present invention, a metabolite containing solution is contacted with a third adsorbent containing column prior to delivery of the metabolite-containing solution to the first and second columns. Preferably, this third column is maintained substantially at the first predetermined temperature.

In a preferred embodiment of the present invention, the adsorbent comprises activated carbon, which is preferably in the form of cylindrical rods of relatively short length.

In accordance with another embodiment to the process of the present invention, the metabolite-containing solution is precooled prior to its delivery to the columns.

In accordance with a preferred embodiment of the present invention the flushing solution comprises the metabolite-containing solution itself.

The disposable tube set in accordance with the present invention for use in connection with a pair of adsorbent-containing columns adapted for the removal of waste metabolites from a metabolite-containing solution comprises a flexible inlet tube for delivery of the metabolite-containing solution to the columns, the flexible inlet tube including a common inlet tube section and first and second inlet tube branches, the first inlet tube branch adapted for connection with the inlet of one of the columns and the second inlet tube branch adapted for connection with the other column, and a flexible outlet tube for removal of the metabolite-containing solution from the columns, the flexible outlet tube including a common outlet tube section and first and second outlet tube branches, the first outlet tube branch adapted for connection with the outlet of one of the columns and the second outlet tube branch adapted for connection with the other column.

In accordance with one embodiment of the disposable tube set of the present invention, means for connecting a third adsorbent-containing column to the common inlet tube section are provided.

In accordance with another embodiment of the present invention each of the first and second outlet tube branches includes an outlet tube collection branch adapted for the removal of a selected portion of the metabolite-containing solution removed from the columns.

In accordance with the preferred embodiment of the disposable tube set of the present invention each of the tube sections are made of plastic.

A BRIEF DESCRIPTION OF THE DRAWINGS

The present invention may be more fully understood with reference to the drawings in which;

FIG. 1 shows a schematic representation of a preferred embodiment of the apparatus and method of the present invention; and FIG. 2 shows a graphical representation of an operation/state/flowt program for the columns of the present invention along a time axis.

DETAILED DESCRIPTION

Figure 1:
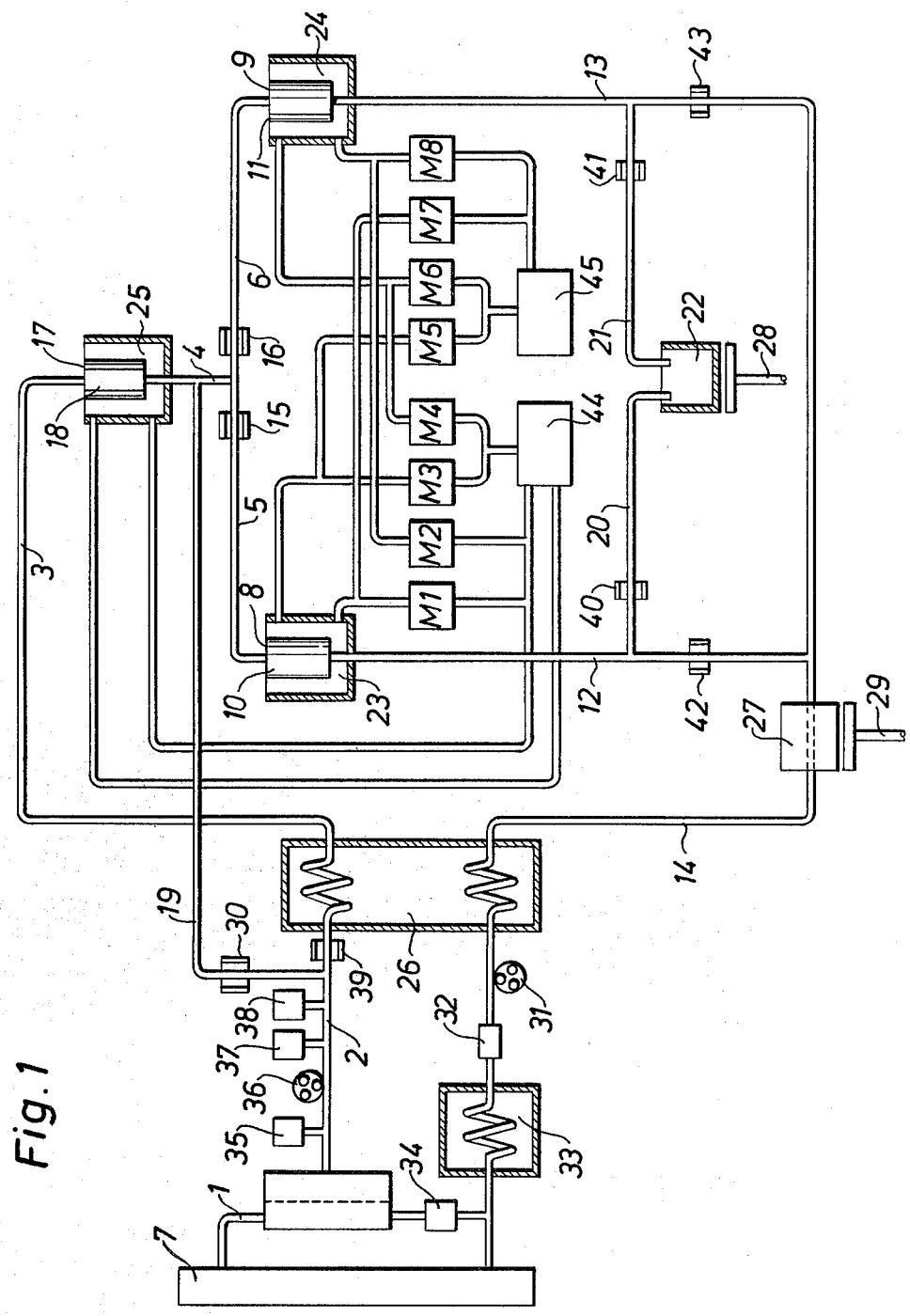

Referring specifically to FIG. 1, the present device comprises a delivery conduit means 1-6, which through a membrane dialyzer or the like is to be connected to a source 7 of the solution which is to be purified by the removal of waste metabolites therefrom, such as a patient himself. Furthermore, the device comprises first and second columns, 8 and 9, respectively, which contain an adsorbent, 10 and 11, respectively, and which are connected to said delivery conduit means for communication therewith, and a withdrawal conduit means, 12-14, for withdrawal of the solution from the first and second columns, 8 and 9. The first column 8 is adapted to be kept at a first lower temperature for adsorption, while the second column 9 is adapted to be kept at a second temperature, which is higher than said first temperature, for desorption, and then these temperatures can be alternated and the respective functions of the columns are reversed. According to the present invention the second column (or whichever column is to be desorbed), is adapted to be warmed for desorption, flushed with a flush solution and then precooled at the same time as the first column is being cooled and used for adsorption.

The delivery conduit means 1-6 includes control means, 15 and 16, preferably valves, in the form of clamps, for alternatingly directing the solution from the delivery conduit means 1-6 into the first and second columns, 8 and 9. In this manner it is possible to perform desorption with essentially non-flowing solution in these columns. In the embodiment shown clamp 15 is provided in an inlet tube 5 of the delivery conduit means, while a second clamp 16 is provided in a corresponding inlet tube 6 of the delivery conduit means to the second column 9.

According to another aspect of the present invention it is preferred that the delivery conduit means 1-6 also include a third column, 17, which contains an adsorbent 18, and which is adapted to be kept essentially at said lower temperature. The third column, 17, which is thus provided before columns 8 and 9, during the whole treatment adsorbs other metabolites, i.e., uric acid, creatinine, phenols, etc., even when saturated with urea. It thus prevents these other metabolites from entering the alternatingly cooled and warmed columns, 8 and 9. Furthermore, column 17 serves to cool the solution before it enters that column of the two columns 8 and 9 which is being used for adsorption.

As the adsorbent activated carbon is preferably used, and advantageously, it is in the shape of short cylindrical rods.

Between the source of the solution 7 and the two columns 8 and 9, a shunt conduit 19 may be coupled to the delivery conduit means in a by-pass relationship with respect to the third column 17. The shunt conduit 19 includes a valve means 30, for example in the form of a clamp, which is co-operable with either one of the clamps 15 and 16 in the inlet tubes, 5 and 6, respectively, so as to direct essentially all solution from the source 7 through the shunt conduit 19 to the first and second columns for flushing after desorption. Spent flush solution is withdrawn through branching conduits 20 and 21, which are coupled to the respective outlet conduit 12 and 13 of the withdrawal conduit means from columns 8 and 9, for collection in a flush liquid container 22.

The columns 8, 9 and 17 may be provided in heat exchanging containers 23, 24 and 25, through which a cooling/warming fluid is adapted to flow for cooling and warming, respectively, of the columns. A cooling fluid is adapted to flow through the heat exchanging container 25 for the third column 17, while a cooling fluid and a warming fluid, respectively, are adapted to alternatingly flow through the heat exchanging containers 23 and 24 for the first and second columns, 8 and 9.

A pre-cooler 26, preferably in the form of a heat exchanger, is provided in the delivery conduit means for cooling the solution. Conveniently, the other side of such a heat exchanger can be attached to the withdrawal conduit means 12-14 for warming the solution in the withdrawal conduit means.

For the sake of safety a buffering liquid storage container 27 may be provided in the withdrawal conduit means 12-14 for storing and keeping a certain buffering amount of the solution. Both the flush liquid collecting container 22 and the buffering liquid storing container 27 are preferably connected to a balance, 28 and 29, respectively, whereby it is possible to monitor the amount of flush solution collected as well as the amount of buffering solution present in container 27.

Preferably, the delivery conduit means 1–6 and the withdrawal conduit means 12–14 are prepared from flexible plastic tubes, whereby it is possible through compression of these tubes by means of clamps 15, 16 and 30 to direct the solution, which will be described in the following.

Alternatively, columns 8, 9 and 17 may be directly warmed and cooled, respectively, i.e., without using any flowing cooling/warming fluid. For example, this can be achieved by means of Peltier elements or the like, which are adapted to directly warm and cool, respectively, the columns. These elements are well-known and are used in other fields for similar heating/cooling purposes, and therefore they do not need to be described in more detail herein.

PREFERRED EMBODIMENT

The most preferred embodiment of the present device, as shown in FIG. 1, comprises first, second and third columns, 8, 9 and 17, respectively, which are in communication with each other through flexible plastic tubes 4–6. The first and second columns, 8 and 9, respectively, are coupled in parallel and connected to the third column 17 via respective inlet tubes, 5 and 6, which constitute branches of a common inlet tube 4 in communication with the outlet of the third column, 17. Outlet tubes 12 and 13, respectively, which constitute branches of a common main outlet tube 14, are connected to the respective outlets of the first and second columns. The outlet tubes 12 and 13 are, in turn, in communication with a common flush liquid collecting container 22 via a second pair of branching tubes, 20 and 21, respectively. The common main outlet tube 14 is adapted to be connected to a source for a solution containing waste metabolites. Between the columns 8 and 9 and the source 7, the main outlet tube 14 is in communication with a buffering solution storage container 27, and the warm side of a heat exchanger 26. Furthermore, prior to its connection with the source 7, main outlet tube 14 may also be in communication with a pump 31, an infusion filter 32, a heater 33 and a bubble trap 34. the components 31–34 are conventional, and therefore need not be described in detail herein.

Similarly, the inlet of the third column 17 is in communication with the source 7 through a common main inlet tube 1–3. Between the source 7 and the third column 17 the common inlet tube 3 is in communication with a manometer 35, a pump 36, a deaerator 37, a blood detector 38 and the cool side of the heat exchanger 26. Again, components 35–38 are conventional and therefore need not be described in detail herein. A shunt conduit means 19 is coupled between the main inlet tube 3 and the inlet tube 4 so as to by-pass the solution pass the heat exchanger 26 as well as the third column 17, as will be described below in more detail.

This apparatus also includes valves in the form of clamps 15, 16, 30 and 40–43, which are adapted to cooperatively open and shut, respectively, the tubes in the device, as will be described.

As is shown in FIG. 1 columns 8, 9 and 17 are contained in heat exchanging containers 23, 24 and 25, respectively, through which a cooling/warming fluid is adapted to flow from a cool source and a warm source, 44 and 45, respectively. The heat exchanging container 25 is thus adapted to be permanently cooled by a cooling fluid from the cool source 44, while heat exchanging containers 23 and 24 are adapted to be alternately cooled and warmed, respectively. The cool source 44 and the warm source 45 are thus in communication with the respective heat exchanging containers through conduits comprising valves M1–M8 which, by suitable controlling, provide for the alternate cooling and warming, respectively, of heat exchanging containers 23 and 24.

The device described above operates in the following manner. During a first period the first and third columns, 8 and 17, respectively, are cooled, as is shown in FIG. 2. Referring specifically to FIG. 2, the following designations are used therein:

A = adsorption
D = desorption
F = flushing
FK = precooling
K = cold
W = warm
R = recirculation of solution
FP = slowing of flush solution (single pass)
V = rest (equals essentially non-flowing solution)

FIG. 2 thus shows operation/state/flow for each of the respective columns on a time basis as shown horizontally thereon. During the first period when the first and third columns are cooled, clamp 30 in shunt conduit means 19, clamp 16 in inlet tube 6, and clamp 40 in branch tube 20, as well as clamps 41 and 43, are closed. The remaining clamps in the device are kept open. The solution from source 7 is pumped by means of pump 36 through heat exchanger 26 and into the cooled, third column 17, where adsorption occurs on activated carbon 18 therein. From column 17 the solution is pumped through main inlet tube 4, through inlet tube 5, and into the first column 8, which is also cooled, and further adsorption occurs on the activated carbon 18 therein. From the first column 8 the solution is pumped by means of pump 31 through outlet tube 12 and back into source 7 via main outlet tube 14 and heat exchanger 26. When the third column 8 is saturated with waste metabolites, urea, etc., the flow of cooling fluid through heat exchanging container 23 is interrupted, and warming fluid from warm source 45 starts to warm column 8. At the same time, clamp 15 in inlet tube 5 is closed, and clamp 16 in inlet tube 6 to the second column is opened. The heat exchanging container 24 is now cooled by cooling fluid from cool source 44 for cooling the second column 9. The solution from source 7 is thus pumped through the third column 17 and the second column 9 through inlet tube 6 and from the second column 9 back into source 7, through outlet tube 13, and common main outlet tube 14. Adsorption now occurs in the second column 9 in the same way as adsorption occurred in the first column 8. During adsorption in the second column 9 the following occurs in the first column 8. As previously mentioned, column 8 is warmed with warming fluid from the warm source 45, whereby desorption occurs in the non-flowing solution within the column 8. As is shown in FIG. 2, the first column 8 is warmed only during a short time period, preferably between 20% and 50%, and at most 75% of the cooling period for the second column 9, whereafter warming of the column 8 is interrupted. In connection with this interruption, clamp 39 in inlet tubes 1–3, and clamp 16 in inlet tube 6 to the second column 9 are closed for a short while. At the same time, clamp 30 in shunt conduit means 19 and clamp 15 in inlet tube 5 to the first column 8 are opened. Furthermore, clamp 42 in outlet tube 12 is closed and clamp 40 in branch tube 20 to the collecting container 22 is opened. During only a minor part of the cooling phase for the second column 9 the solution is pumped from source 7 directly into the first column 8 via shunt conduit means 19. Said solution, which serves as flush solution for the first column 8, is then pumped through outlet tube 12, and is collected in the flush liquid collecting container 22 via branch tube 20. The amount of flush solution employed during desorption will thus preferably not be substantially greater than the volume of solution contained in the column 8 in the spaces between the activated carbon 10. Clamp 15 in inlet tube 5 to the first column 8, as well as clamp 30 in shunt conduit means 19, are then again closed, while clamp 39 in inlet tubes 1-3, and clamp 16 in inlet tube 6, to the second column 9, are opened, whereby solution from the source 7 during the remaining adsorption phase for the column 9 continues to flow through the third column 17 and the second column 9 back to the source 7. During this remaining adsorption phase the first column 8 is cooled, as is shown in FIG. 2, by cooling fluid from the cool source 44 so that it becomes cool enough for a new adsorption phase to take place in column 8 when said adsorption phase has ended. When the second column 9 is saturated with waste metabolites, urea, etc. clamp 16 in inlet tube 6 t the second column 9 is thus closed, while clamp 15 in inlet tube 5 to the first column 8 is opened. At the same time, the flow of cooling fluid through the heat exchange container 24 is interrupted, and heat exchange container 24 is warmed with warming fluid from warm source 45. The solution from the source 7 is pumped through the third column 17 and the first column 8 for adsorption, and then back to the source 7, while the volume of solution present in the second column 9 within the space between the particles of activated carbon 18 is kept non-flowing and is warmed for desorption in the same way as described hereinabove. The alternating cooling, warming and flushing of the columns 8 and 9 is continued until a predetermined amount of waste metabolites, urea, etc. has been collected in the flush liquid collecting container 22. The present invention may be further understood by reference to the following working example thereof.

EXAMPLE

In this example four experiments were carried out in order to study the removal of waste metabolites, especially urea, from a hemofiltrate containing such metabolites, by use of the process and device of the present invention as described in detail above. In the respective experiments either short and thick columns (as in experiments 1 and 2) or long and narrow columns (as in experiments 3 and 4) were used. For the short columns, longer cycle times were used, and for the longer columns, shorter cycle times were used. These cycle times, as well as other conditions, are set forth in Table I. It is, however, to be noted that the total treatment time for each experiment was within the period of from 3 to 4 hours.

The used hemofiltrate solution, which was buffered with either acetate or bicarbonate, had the following content of electrolytes:

TABLE I

| acetate - hemofiltrate | | bicarbonate - hemofiltrate | |
|---|---|---|---|
| $Na^+$ | 132.0 mval/l | $Na^+$ | 135.0 mval/l |
| $K^+$ | 3.0 mval/l | $K^+$ | 6.0 mval/l |
| $Ca^{2+}$ | 3.5 mval/l | $Ca^{2+}$ | 3.0 mval/l |
| $Mg^{2+}$ | 1.5 mval/l | $Mg^{2+}$ | 2.0 mval/l |
| $Cl^-$ | 105.0 mval/l | $Cl^-$ | 116.0 |
| $Ac^-$ | 35.0 mval/l | $SO_4^{2-}$ | 1.5 mval/l |
| | | $PO_4^{3-}$ | 3.5 mval/l |
| | | $HCO_3^-$ | 25.0 mval/l |

Both the original and the final concentrations of urea are set forth in Table II.

The hemofiltrate was passed through the device at a rate of 100 ml/min., and before entering into the third column, which was cooled with cooling fluid to about 0° C., it was pre-cooled, and then continued to be cooled in one of the two additional columns, which were used for adsorption, and which were also kept near 0° C. by cooling fluid during such use. The other of these two columns was thus warmed to between 60° and 80° C. for desorption. After leaving the columns, but before returning to the source, the temperature of the hemofiltrate was set at near 37° C., which was the original temperature of the hemofiltrate.

TABLE II

| Experiment: | 1 | 2 | 3 | 4 |
|---|---|---|---|---|
| Column: | | | | |
| length, cm | 32 | 30 | 175 | 175 |
| diameter, cm | 3.8 | 3.8 | 1.5 | 1.5 |
| Carbon: | | | | |
| type | cylindrical rods | spherical | cylindrical rods | cylindrical rods |
| total amount, g | 3 × 165 | 3 × 165 | 3 × 120 | 3 × 120 |
| Cycle time: | | | | |
| precooling, min. | 7 | 7 | 7 | 7 |
| adsorption, min. | 20 | 20 | 15 | 15 |
| desorption, min. | 10 | 10 | 5 | 5 |
| flushing, min. | 3 | 3 | 3 | 3 |
| total treatment time, hrs. | 3¼ | 3¼ | 4 | 4 |
| number of flushings | 8 | 8 | 14 | 14 |
| Hemofiltrate, l. | 18 | 18 | 36 | 18 |
| type | acetate | acetate | bicarbonate | bicarbonate |
| flush solution, l. | 2.2 | 2.3 | 4.2 | 4.2 |
| Urea, mg % hemofiltrate (original) | 251 | 254 | 248 | 252 |
| hemofiltrate (final) | 176 | 175 | 195 | 165 |
| flush solution | 347 | 372 | 396 | 362 |
| total amount of removed urea, g. | 18.0 | 18.4 | 28.0 | 23.2 |
| $K^+$ original concentration in hemofiltrate, mval/l. | 3.0 | 3.0 | 6.1 | — |
| final concentration in hemofiltrate, mval/l. | 2.6 | 2.5 | 6.1 | — |

As is shown by the results in Table II, in practically all of the experiments between 20 and 30 grams of urea was removed from the used hemofiltrate within the period of between 3 and 4 hours, without more than 4 liters of hemofiltrate having to be withdrawn and wasted. Furthermore, it was also possible to remove $K^+$, as is shown in experiments 1 and 2. Even though the amount of urea which was removed in experiments 1 and 2 was slightly less than 20 grams (18.0 and 18.4 grams, respectively) this difference could possibly be increased to the desired amount of between 20 and 30 grams by increasing the treatment time, which was shorter than 4 hours in these experiments.

Finally, it is to be noted that the process and apparatus according to the present invention demonstrates further technical progress over the prior art, and in particular makes it possible to remove waste metabolites, including $K^+$, within a substantially shorter time period and by the use of substantially smaller volumes of solution than has previously been possible.

INDUSTRIAL APPLICABILITY

As preferred use of the present invention is for the removal of waste metabolites, especially nitrogenous poisons such as urea, from hemofiltrate or dialysis solution withdrawn from a patient suffering from uremia. In that case, the hemofiltrate will be pumped with a flow rate of about 100 ml. a minute through three columns, which are packed with activated carbon, with the third column being continuously cooled, while the first and second columns are alternately cooled and warmed, for adsorption and desorption, respectively. The adsorption time (cooling) conveniently is about 20 minutes, while the desorption time (warming) is about 10 minutes. The remaining 10 minutes, during which the adsorption continues in one of said first and second columns, the other of said first and second columns is exposed to a flushing phase (about 3 minutes) and a pre-cooling phase (about 7 minutes). The total treatment time varies between about 3 and 4 hours.

What is claimed is:

1. A process for the removal of waste metabolites from a metabolite-containing solution by alternately adsorbing and desorbing said metabolites on an adsorbent contained in a plurality of columns, said process coprising alternately delivering said metabolite-containing solution to said first and second adsorbent-containing columns so as to alternately adsorb and desorb said metabolites on said adsorbent in said first and second columns, respectively, said metabolites being adsorbed on said adsorbent during said delivery of said metabolite-containing solution to said columns, and said metabolite-containing solution remaining in contact with said adsorbent during said desorption of said columns, maintaining said first and second columns, respectively, at a first predetermined temperature during said adsorption of said metabolites on said adsorbent, maintaining said first and second columns, respectively, at a second predetermined temperature during said desorption of said metabolite from said adsorbent, said first predetermined temperature being lower than said second predetermined temperature so as to increase the effectiveness of said adsorbent for adsorption of said metabolites therein at said first predetermined temperature, flushing said first and second columns, respectively, with a flushing solution subsequent to desorption of said columns, and terminating the flow of said metabolite-containing solution to said first and second columns, respectively, prior to flushing said columns so that desorption of said columns is carried out substantially without the flow of liquid therein.

2. The process of claim 1 including lowering said second predetermined temperature subsequent to desorbing said columns so as to pre-cool said columns prior to adsorption of said metabolite in said first and second columns, respectively.

3. The process of claim 1 wherein said first and second columns, respectively, are maintained at said first predetermined temperature for a first predetermined time period and said first and second columns, respectively, are maintained at said second predetermined temperature for a second predetermined time period, said second predetermined time period being shorter than said first predetermined time period.

4. The process of claim 3 wherein said second predetermined time period is less than about 75% of said first predetermined time period.

5. The process of claim 3 wherein said second predetermined time period is from about 20% to 50% of said first predetermined time period.

6. The process of claim 1 wherein only a minor portion of said metabolite-containing solution contacts said adsorbent during said desorption of said columns.

7. The process of claim 1 including contacting said metabolite-containing solution with a third adsorbent-containing column prior to said delivery of said metabolite-containing solution to said first and second columns.

8. The process of claim 7 including maintaining said third column substantially at said first predetermined temperature.

9. The method of claim 1 or 7 wherein said adsorbent comprises activated carbon.

10. The process of claim 9 wherein said activated carbon is in the form of cylindrical rods.

11. The process of claim 1 including pre-cooling said metabolite-containing solution prior to delivery of said metabolite-containing solution to said first and second columns, respectively.

12. The process of claim 1 wherein the flushing solution comprises said metabolite-containing solution.

* * * * *

UNITED STATES PATENT AND TRADEMARK OFFICE
CERTIFICATE OF CORRECTION

PATENT NO. : 4,313,831
DATED : Feb. 2, 1982
INVENTOR(S) : Hans-Dieter Lehmann; Lars-Ake Larsson It is certified that error appears in the above-identified patent and that said Letters Patent are hereby corrected as shown below:

Column 10, line 6,

" $Cl^-$   105.0 mval/l   $Cl^{-116.0}$ "

should read

-- $Cl^-$   105.0 mval/l   $Cl^-$   116.0 mval/l --

[SEAL]

Attest:

Attesting Officer

Signed and Sealed this

Twentieth Day of July 1982

GERALD J. MOSSINGHOFF

Commissioner of Patents and Trademarks